(12) United States Patent
Katsuki et al.

(10) Patent No.: US 7,928,257 B2
(45) Date of Patent: Apr. 19, 2011

(54) METHOD FOR PRODUCING OPTICALLY ACTIVE AZIRIDINE COMPOUNDS AND AMINE COMPOUNDS AS WELL AS COMPLEXES AND THEIR INTERMEDIATES USED IN THIS METHOD

(75) Inventors: Tsutomu Katsuki, Fukuoka (JP); Kazufumi Omura, Minamiashigara (JP); Tatsuya Uchida, Fukuoka (JP); Ryo Irie, Fukuoka (JP)

(73) Assignee: Japan Science and Technology Agency, Kawaguchi-Shi (JP)

( * ) Notice: Subject to any disclaimer, the term of this patent is extended or adjusted under 35 U.S.C. 154(b) by 0 days.

(21) Appl. No.: 12/654,824

(22) Filed: Jan. 5, 2010

(65) Prior Publication Data

US 2010/0113815 A1     May 6, 2010

Related U.S. Application Data

(62) Division of application No. 11/631,166, filed as application No. PCT/JP2005/011059 on Jun. 16, 2005, now Pat. No. 7,754,899.

(30) Foreign Application Priority Data

Jul. 2, 2004 (JP) ................................. 2004-197255

(51) Int. Cl.
*C07F 15/00* (2006.01)
*C07C 211/09* (2006.01)

(52) U.S. Cl. ........................................ 556/137; 564/337

(58) Field of Classification Search .................. 556/137; 564/337
See application file for complete search history.

(56) References Cited

FOREIGN PATENT DOCUMENTS
EP   1 449 831 A1   8/2004
JP   A-2002-080415   3/2002

OTHER PUBLICATIONS

Kawabata et al., "Construction of Robust Ru-Salen Complex and Asymmetric Aziridination with Azide Compounds as Nitrene Precursor," *The Chemical Society of Japan*, vol. 85, No. 2, Mar. 11, 2005, p. 1091. (w/ Abstract).
Omura et al., "Design of a robust Ru(salen) complex: aziridination with improved turnover number using N-arylsulfonyl azides as precursors," *Chemical Communications*, No. 18, Sep. 21, 2004, pp. 2060-2061.
Omura et al., "Asymmetric Aziridnation and Regioselective Amination Using Azide Compound as a Nitrene Precursor," vol. 36, Oct. 20, 2003, pp. 50-52. (w/ Abstract).
Hamada et al., "Highly Enantioselective Benzylic Hydroxylation with Concave Type of (Salen)manganese(III) Complex," *Tetrahedron*, vol. 54 (1998), pp. 10017-10028.
Murakami et al. "Ru(salen)-catalyzed asymmetric sulfimidation using arylsulfonyl azide." *Tetrahedron Letters*. vol. 42 (2001), pp. 7071-7074.
Murakami et al. "Ru(salen)-Catalyzed Asymmetric Sulfimidation and Subsequent [2,3]Sigmatropic Rearrangement." *Chirality*. vol. 15 (2003), pp. 116-123.
Omura et al. "Enantioselective Aziridination and Amination Using p-Toluenesulfonyl Azide in the Presence of Ru(salen)(CO) Complex." *Chemistry Letters*. vol. 32, No. 4 (2003), pp. 354-355.
Sasaki et al., "Rational Design of Mn-Salen Catalyst (2): Highly Enantioselective Epoxidation of Conjugated *cis*-Olefins," *Tetrahedron*, vol. 50, No. 41, pp. 11827-11838 (1994).
Uchida, Tatsuya et al. "Mechanism of asymmetric Sulfimidation with N-alkoxycarbonyl azide in the presence of (OC)Ru(salen) complex," Crest, Oct. 20, 2003, pp. 7965-7968, vol. 44, No. 43, *Tetrahedron Letters*, Elsevier, Amsterdam.
Apr. 27, 2010 Office Action issued in Japanese Patent Application No. 2006-528490 (with translation).
The Chemical Society of Japan, The 83rd Annual Spring Meeting (2003), Seminar Proceeding II, 2003, p. 1199.

*Primary Examiner* — Joseph R Kosack
(74) *Attorney, Agent, or Firm* — Oliff & Berridge, PLC

(57) ABSTRACT

This invention provides a method for producing an optically active aziridine compound or amine compound, which uses as a catalyst a Ru(salen)(CO) complex represented by the following formula (I) or its enantiomer having a high stability, in a high turnover number (TON) and a high enantioselectivity. In the formula (I), Ar is represented by the following formula (VI) or (VII), wherein in the formula (VI), Xs are independently a halogen or a halogenated alkyl group and $R^1$ and $R^2$s are independently hydrogen or an alkyl group or a trialkylsilyl group having a carbon number of 1-4, and in the formula (VII), $R^3$ is a bulky group.

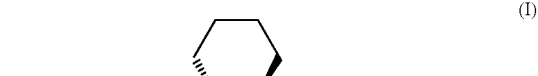

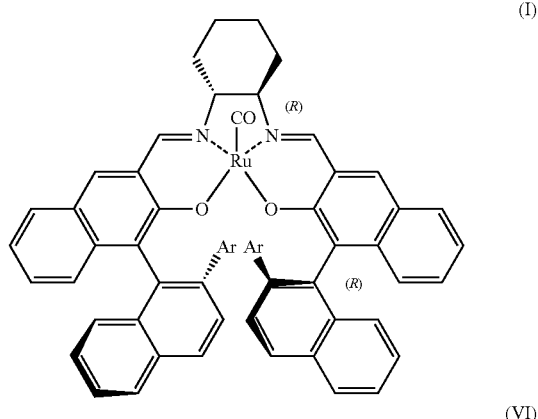

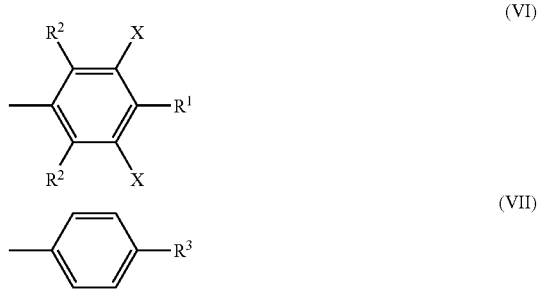

4 Claims, 1 Drawing Sheet

METHOD FOR PRODUCING OPTICALLY ACTIVE AZIRIDINE COMPOUNDS AND AMINE COMPOUNDS AS WELL AS COMPLEXES AND THEIR INTERMEDIATES USED IN THIS METHOD

This is a Division of application Ser. No. 11/631,166, filed Jan. 22, 2007, which in turn is a National Stage of Application No. PCT/JP2005/011059, filed Jun. 16, 2005, which claims priority to Japanese Patent Application No. 2004-197255, filed Jul. 2, 2004. The disclosures of the prior applications are hereby incorporated by reference herein in their entirety.

TECHNICAL FIELD

This invention relates to a method for producing optically active aziridine compounds and amine compounds as well as complexes and their intermediates used in this method, and more particularly to a method for producing an optically active aziridine compound or amine compound by subjecting an olefin to an asymmetric aziridination or an asymmetric amination with a Ru(salen)(CO) complex of a specific structure as a catalyst.

BACKGROUND ART

The transfer of nitrene is a fundamental C—N bond formation reaction. It is well-known that many metal complexes function as a catalyst for the nitrene transfer reaction through a metal nitrenoid intermediate, and much efforts have been directed to an asymmetric nitrene transition reaction, especially aziridination and amination. Chiral metal complexes such as metalloporphyrins, metallosalens, Cu-bis(oxazoline), Cu-bis(Schiff base), Cu-diamine complexes and the like have been examined as a catalyst for the asymmetric nitrene transition reaction, and reported to have a high enantio-selectivity.

In the above reports, however, N-arylsulfonyliminophenyl iodinane (PhI=NSO$_2$Ar) has been used as a nitrene precursor. In this case, there are problems that iodobenzene is yielded as a by-product and it is difficult to remove an arylsulfonyl group from a product.

On the other hand, there is reported an asymmetric nitrene transfer reaction using N-arylsulfonyl azide instead of N-arylsulfonyliminophenyl iodinane, but the enantio-selectivity in this reaction is insufficient or the severe reaction condition such as UV-irradiation, heating or the like is required for promoting the nitrene transfer reaction.

On the contrary, the inventors have reported that it is possible to conduct an asymmetric sulfimidation of an alkyl aryl sulfide and asymmetric aziridination and amination of an olefin with N-arylsulfonyl azide as a nitrene precursor at room temperature in the presence of a Ru(salen)(CO) complex without photo-irradiation (see Literature 1: M. Murakami, T. Uchida, T. Katsuki, Tetrahedron Lett., 2001, 42, 7071-7074, Literature 2: M. Murakami, T. Uchida, B. Saito, T. Katsuki, Chirality, 2003, 15, 116-123, and Literature 3: K. Omura, M. Murakami, T. Uchida, R. Irie, T. Katsuki, Chem. Lett., 2003, 32, 354-355).

DISCLOSURE OF THE INVENTION

However, when the Ru(salen)(CO) complex described in the above Literatures 1-3 is used as a catalyst, since the stability of the Ru(salen)(CO) complex is low, the turnover number (TON) of the catalyst is small and there is a problem in view of industrialization.

It is, therefore, an object of the invention to solve the above-mentioned problems of the conventional techniques and to provide a method for producing an optically active aziridine compound or amine compound, which uses as a catalyst a Ru(salen)(CO) complex having a high stability and a specified structure and has a high turnover number (TON) and a high enantioselectivity. Moreover, it is another object of the invention to provide a Ru(salen)(CO) complex having the specified structure and being suitable as the catalyst in the above production method as well as intermediates and salen ligands used in the synthesis of the complex.

The inventors have made various studies in order to achieve the above objects and discovered that the stability of the complex is improved and the turnover number (TON) is increased by introducing a halogen, a halogenated alkyl or a bulky group into the salen ligand of the Ru(salen)(CO) complex to make the complex have the specified structure, whereby the optically active aziridine compound or amine compound can be produced more economically, and as a result the invention has been accomplished.

That is, the method for producing an aziridine compound according to the invention is characterized by using as a catalyst an optically active Ru(salen)(CO) complex represented by the following formula (I) or (II) and subjecting an olefin represented by the following formula (III) to an asymmetric aziridination with a sulfonyl azide compound represented by the following formula (IV), and can produce an optically active aziridine compound represented by the following formula (V).

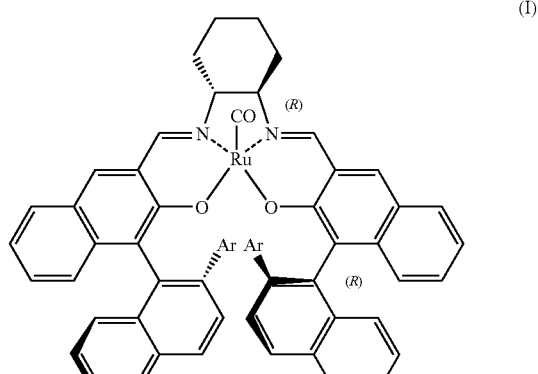

(I)

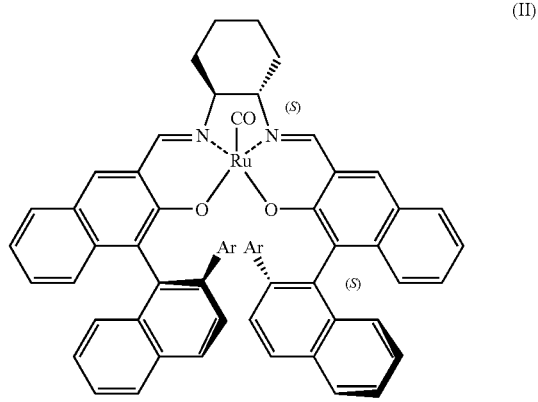

(II)

[in the formulae (I) and (II), Ars are represented by the following formula (VI) or (VII):

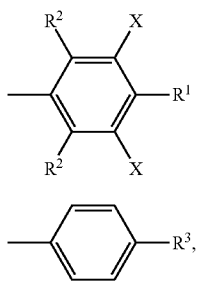

(VI)

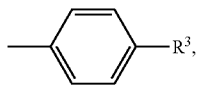

(VII)

in the formula (VI), Xs are independently a halogen or a halogenated alkyl group, and $R^1$ and $R^2$s are independently hydrogen or an alkyl group or a trialkylsilyl group having a carbon number of 1 to 4, and in the formula (VII), $R^3$ is a bulky group.]

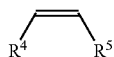

(III)

[wherein $R^4$ is an alkyl group or a substituted alkyl group having a carbon number of 1 to 15, an alkenyl group or a substituted alkenyl group having a carbon number of 2 to 20, an alkynyl group or a substituted alkynyl group having a carbon number of 2 to 20, or an aryl group or a substituted aryl group having a carbon number of 6 to 20, $R^5$ is hydrogen or an alkyl group or a substituted alkyl group having a carbon number of 1 to 10, with the proviso that $R^4$ and $R^5$ may be bonded with each other to form a ring.]

$R^6$—$SO_2N_3$ (IV)

[wherein $R^6$ is an alkyl group, a substituted alkyl group, an aryl group or a substituted aryl group.]

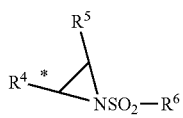

(V)

[wherein each of $R^4$, $R^5$ and $R^6$ is the same meaning as mentioned above.]

In the method for producing the optically active aziridine compound according to the invention, when Ar is represented by the formula (VI), it is preferable that Xs are fluorine or chlorine, $R^1$ is a methyl group or a trimethylsilyl group and $R^2$s are hydrogen in the formula (VI). Also, when Ar is represented by the formula (VII), it is preferable that $R^3$ in the formula (VII) is a group formed by bonding three alkyl groups or aryl groups to carbon or silicon.

In a preferable embodiment of the method for producing the optically active aziridine compound according to the invention, $R^4$ is selected from the group consisting of phenyl group, p-bromophenyl group, p-nitrophenyl group, 2-naphthyl group, phenylethynyl group and n-hexyl group, and $R^5$ is hydrogen in the olefin represented by the formula (III).

In another preferable embodiment of the method for producing the optically active aziridine compound according to the invention, the olefin represented by the formula (III) is indene.

In the other preferable embodiment of the method for producing the optically active aziridine compound according to the invention, the sulfonyl azide compound represented by the formula (IV) is toluenesulfonyl azide, nitrobenzenesulfonyl azide or trimethylsilylethanesulfonyl azide.

On the other hand, the method for producing an amine compound according to the invention is characterized by using as a catalyst the optically active Ru(salen)(CO) complex represented by the above formula (I) or (II) in which Ar is represented by the above formula (VI) and subjecting an olefin represented by the following formula (VIII) to an asymmetric amination with the sulfonyl azide compound represented by the above formula (IV), and can produce an optically active amine compound represented by the following formula (IX).

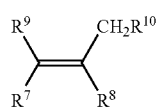

(VIII)

[wherein $R^7$, $R^8$ and $R^9$ are hydrogen, an alkyl group or a substituted alkyl group having a carbon number of 1 to 20, or an aryl group or a substituted aryl group having a carbon number of 6 to 15, with the proviso that at least one of $R^7$ and $R^8$ is not hydrogen, and $R^{10}$ is an alkyl group or a substituted alkyl group having a carbon number of 1 to 20, and $R^7$ and $R^8$ as well as $R^9$ and $R^{10}$ may be bonded with each other to form a ring.]

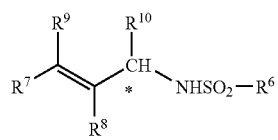

(IX)

[wherein each of $R^6$, $R^7$, $R^8$, $R^9$ and $R^{10}$ is the same meaning as mentioned above.]

In a preferable embodiment of the method for producing the optically active amine compound according to the invention, X is fluorine or chlorine, $R^1$ is a methyl group or a trimethylsilyl group and $R^2$ is hydrogen in the Ru(salen)(CO) complex represented by the formula (I) or (II) in which Ar is represented by the formula (VI).

In another preferable embodiment of the method for producing the optically active amine compound according to the invention, the olefin represented by the formula (VIII) is represented by the following formula (X).

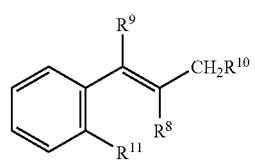

(X)

[wherein each of $R^8$, $R^9$ and $R^{10}$ is the same meaning as mentioned above, $R^{11}$ is hydrogen or an alkyl group or a substituted alkyl group having a carbon number of 1 to 20, with the proviso that $R^8$ and $R^{11}$ as well as $R^9$ and $R^{10}$ may be bonded with each other to form a ring.] At this point, as the olefin represented by the formula (X) are mentioned 1-phenylcyclopentene and 2-ethylindene.

In the other preferable embodiment of the method for producing the optically active amine compound according to the invention, the sulfonyl azide compound represented by the formula (IV) is toluenesulfonyl azide, nitrobenzenesulfonyl azide or trimethylsilylethanesulfonyl azide.

Also, the Ru(salen)(CO) complex according to the invention is represented by the above formula (I) or (II) and is suitable as a catalyst for the production of the aziridine compound and the amine compound. At this point, it is preferable that Ar is represented by the above formula (VI) in which Xs are fluorine or chlorine, $R^1$ is a methyl group or a trimethylsilyl group and $R^2$s are hydrogen. It is also preferable that Ar is represented by the above formula (VII) in which $R^3$ is a group formed by bonding three alkyl groups or aryl groups to carbon or silicon.

Moreover, the intermediate according to the invention is represented by the following formula (XI) or (XII):

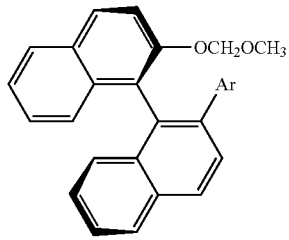

(XI)

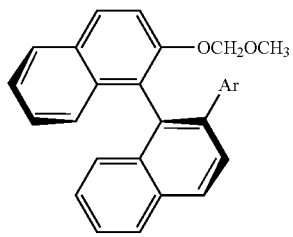

(XII)

[in the formulae (XI) and (XII), Ar is represented by the above formula (VI)], the following formula (XIII) or (XIV):

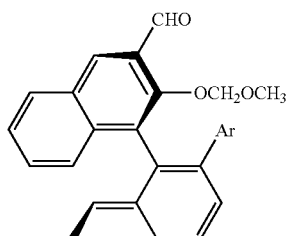

(XIII)

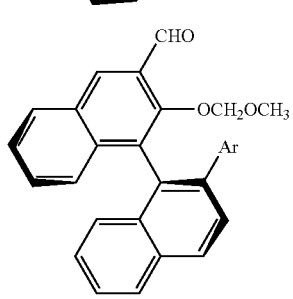

(XIV)

[in the formulae (XIII) and (XIV), Ar is represented by the above formula (VI).] or the following formula (XV) or (XVI):

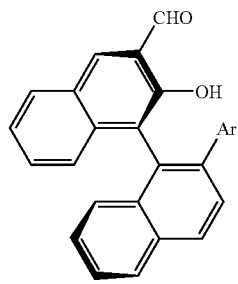

(XV)

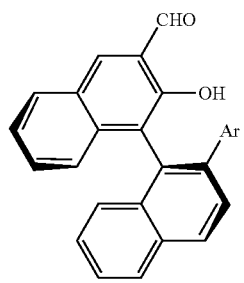

(XVI)

[in the formulae (XV) and (XVI), Ar is represented by the above formula (VI)].

Furthermore, the salen ligand according to the invention is represented by the following formula (XVII) or (XVIII).

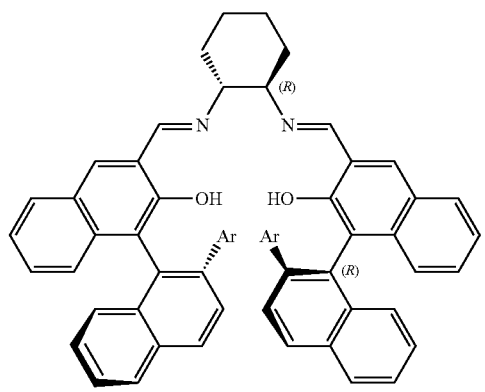

(XVII)

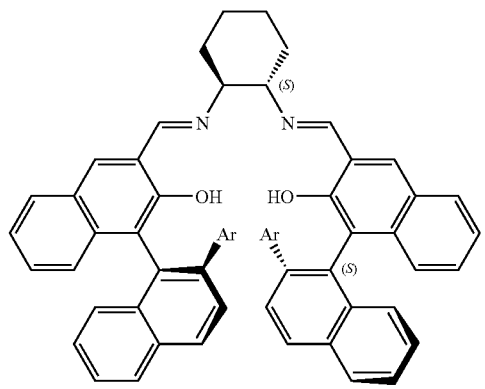

(XVIII)

[in the formulae (XVII) and (XVIII), Ars are represented by the above formula (VI).]

According to the invention, the optically active aziridine compounds and amine compounds can be produced with a high turnover number and a high enantioselectivity by using the sulfonyl azide compound as the nitrene precursor.

BEST MODE FOR CARRYING OUT THE INVENTION

Figure 1:
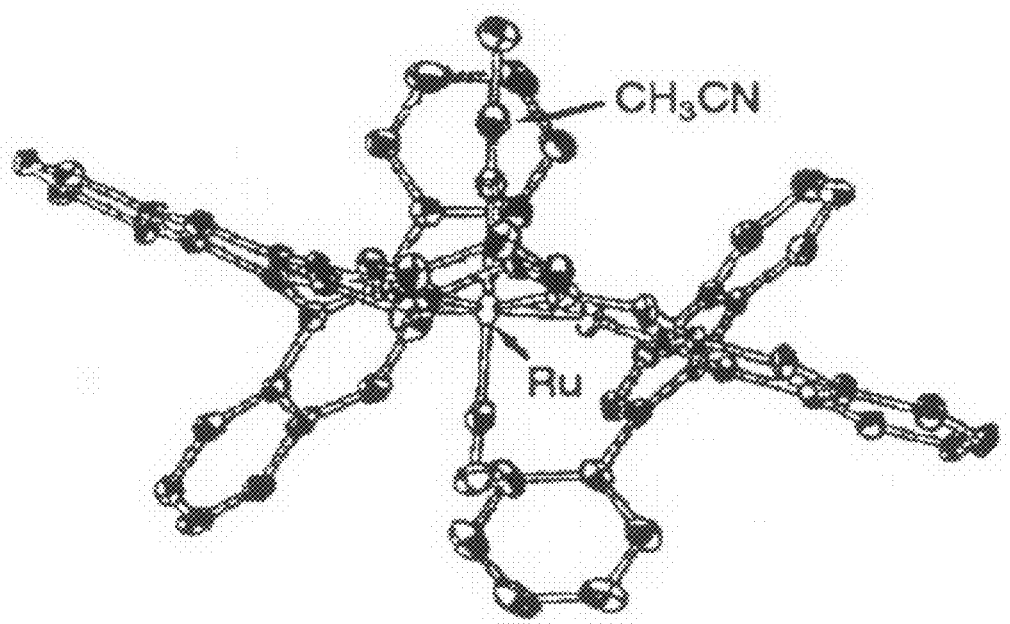
FIG. 1 shows a result of X-ray structure analysis of a crystal obtained by recrystallizing the Ru(salen)(CO) complex described in the above Literatures 1-3 from acetonitrile.

The methods for producing the optically active aziridine compounds and amine compounds according to the invention will be explained in detail below. The optically active Ru(salen)(CO) complex used as a catalyst in the invention is represented by the formula (I) or (II). The complex of the formula (II) is an enantiomer of the complex of the formula (I). In the formulae (I) and (II), Ar is represented by the formula (VI) or (VII). In the formula (VI), Xs are independently halogen or a halogenated alkyl group. As the halogen are mentioned fluorine, chlorine, bromine and iodine, and among them fluorine and chlorine are preferable. As the halogenated alkyl group are mentioned perfluoroalkyl groups such as trifluoromethyl group and so on, and its carbon number is preferable to be within a range of 1 to 4. Moreover, in the formula (VI), $R^1$ and $R^2$s are independently hydrogen or an alkyl group or a trialkylsilyl group having a carbon number of 1 to 4. As the alkyl group are mentioned methyl group, ethyl group and so on, and as the trialkylsilyl group are mentioned trimethylsilyl group, ethyldimethylsilyl group and so on. Furthermore, in the formula (VII), $R^3$ is a bulky group. The bulky group is not particularly limited as far as it can suppress the drawing of hydrogen atoms at its neighboring 3-position and 5-position. As the bulky group is preferably mentioned a group formed by bonding three alkyl groups or aryl groups to carbon or silicon, i.e. a group represented by the formula of —$SiR^{12}_3$ or —$CR^{12}_3$ [wherein $R^{12}$s are independently an alkyl group or an aryl group]. As the alkyl group bonded to carbon or silicon is preferable an alkyl group having a carbon number of 1 to 4 such as methyl group, ethyl group, n-propyl group, i-propyl group, n-butyl group, i-butyl group, sec-butyl group, t-butyl group or the like. As the aryl group bonded to carbon or silicon is preferable an aryl group having a carbon number of 6 to 7 such as phenyl group, tolyl group or the like. As $R^3$ in the formula (VII) are concretely mentioned t-butyldimethylsilyl group, t-butyldiphenylsilyl group, triethylsilyl group, t-butyl group and so on. In view of the synthesis of the complex, it is preferable that $R^1$ is methyl group or trimethylsilyl group and $R^2$s are hydrogen in the Ru(salen)(CO) complex represented by the formula (I) or (II) in which Ar is represented by the formula (VI). Moreover, these Ru(salen)(CO) complexes have a CO ligand at its apical position. The amount of the Ru(salen)(CO) complex used as a catalyst is within a range of 0.01 to 100 mol %, preferably 0.1 to 4 mol % per the molar amount of the olefin as a substrate.

As a result of the inventors' X-ray structure analysis of the Ru(salen)(CO) complex described in the Literatures 1-3 recrystallized from acetonitrile, it has been discovered that carbons at a meta-position of phenyl group in 2-phenylnaphthyl group at 3 or 3'-position is very close (3.59 Å) to a nitrogen atom of the acetonitrile bonded to ruthenium as shown in FIG. 1. Since the acetonitrile bonded to ruthenium is replaced with the sulfonyl azide compound during the reaction, it is considered that the carbon at the meta-position will be preferentially aminated by the sulfonyl azide compound bonded to ruthenium.

On the contrary, in the Ru(salen)(CO) complex represented by the formula (I) or (II) in which Ar is represented by the formula (VI), since Xs are bonded to the carbons at the meta-position of the phenyl group in the 2-phenylnaphthyl group at the 3 or 3'-position to prevent the amination with the sulfonyl azide compound, the stability during the reaction is high and the turnover number (TON) can be improved. Also, in the Ru(salen)(CO) complex represented by the formula (I) or (II) in which Ar is represented by the formula (VII), since the bulky group at the para-position protects hydrogen at the adjoining meta-position from the amination with the sulfonyl azide compound, the stability during the reaction is high and the turnover number (TON) can be improved.

The optically active Ru(salen)(CO) complex represented by the formula (I) in which Ar is represented by the formula (VI) can be synthesized by substituting an iodine of the well-known (R)-2'-iodo-2-methoxymethoxy-1,1'-binaphtyl with a substituted phenyl group represented by the formula (VI) to obtain an intermediate represented by the formula (XI), formylating the intermediate represented by the formula (XI) to obtain an intermediate represented by the formula (XIII), hydrolyzing the intermediate represented by the formula (XIII) to obtain an intermediate represented by the formula (XV), obtaining a salen ligand represented by the formula (XVII) from the intermediate represented by the formula (XV) and (1R,2R)-1,2-diaminocyclohexane, and coordinating the salen ligand represented by the formula (XVII) to a ruthenium compound such as triruthenium dodecacarbonyl.

Similarly, the optically active Ru(salen)(CO) complex represented by the formula (II) in which Ar is represented by the formula (VI) can be synthesized by substituting an iodine of the well-known (S)-2'-iodo-2-methoxymethoxy-1,1'-binaphtyl with a substituted phenyl group represented by the formula (VI) to obtain an intermediate represented by the formula (XII), formylating the intermediate represented by the formula (XII) to obtain an intermediate represented by the formula (XIV), hydrolyzing the intermediate represented by the formula (XIV) to obtain an intermediate represented by the formula (XVI), obtaining a salen ligand represented by the formula (XVIII) from the intermediate represented by the formula (XVI) and (1S,2S)-1,2-diaminocyclohexane, and coordinating the salen ligand represented by the formula (XVIII) to the ruthenium compound.

The sulfonyl azide compound used as a nitrene precursor in the invention is represented by the formula (IV). In this formula, $R^6$ is an alkyl group, a substituted alkyl group, an aryl group or a substituted aryl group. At this moment, carbon numbers of the alkyl group and the substituted alkyl group are preferably within a range of 1 to 20, and carbon numbers of the aryl group and the substituted aryl group are preferably within a range of 6 to 20. Moreover, as the substituent in the substituted alkyl group and the substituted aryl group are mentioned a halogen atom such as chlorine, bromine or the like, an alkoxy group having a carbon number of 1 to 4 such as methoxy group, ethoxy group, propoxy group, butoxy group or the like, a trialkylsilyl group having a carbon number of 3 to 12 such as trimethylsilyl group or the like, a nitro group and so on. As the sulfonyl azide compound are concretely mentioned substituted or non-substituted arylsulfonyl azides such as p-toluenesulfonyl azide (p-$CH_3C_6H_4SO_2N_3$), p-nitrobenzenesulfonyl azide (p-$O_2NC_6H_4SO_2N_3$), o-nitrobenzenesulfonyl azide (o-$O_2NC_6H_4SO_2N_3$), p-methoxybenzenesulfonyl azide (p-$CH_3OC_6H_4SO_2N_3$), p-bromobenzenesulfonyl azide (p-$BrC_6H_4SO_2N_3$) and the like, and substituted or non-substituted alkylsulfonyl azides such as 2-trimethylsilylethanesulfonyl azide (($CH_3)_3SiCH_2CH_2SO_2N_3$) and the like. Among them, p-toluenesulfonyl azide, p-nitrobenzenesulfonyl azide and 2-trimethylsilylethanesulfonyl azide are particularly preferable. Moreover, when the complex represented by the formula (I) or (II) in which Ar is represented by the formula (VI) in which Xs are a halogen except for chlorine or a halogenated alkyl group as well as the complex represented by the formula (I) or (II) in which Ar is represented by the formula (VII) are used as the catalyst, it is preferable to use an arylsulfonyl azide compound in which $R^6$ is the aryl group or the substituted aryl group. These sulfonyl azide compounds can be easily prepared from a commercially available sulfonyl chloride at one step [which is described, for example, on page 505 of "Organic synthesis experiment handbook" published by Maruzen]. The amount of the sulfonyl azide compound used is within a range of 1 mol to 3 mol, preferably 1 mol to 1.5 mol per 1 mol of the after-mentioned olefin as a substrate. From a viewpoint that the yield is increased, it is preferable that the molar amount of the sulfonyl azide compound is made somewhat excess as compared with that of the olefin.

In the conventional nitrene transfer reaction is used a nitrene precursor such as arylsulfonyliminophenyliodinane ($ArSO_2N{=}IPh$) or the like, the synthesis of which being complicated. On the contrary, according to the invention, an easily synthesizable sulfonyl azide ($R^6SO_2N_3$) is used as the nitrene precursor, so that there are advantages that the production process can be simplified and the cost can be reduced. Moreover, p-nitrobenzenesulfonyl azide and o-nitrobenzenesulfonyl azide can be used in the invention, and in this case there is an advantage that o- or p-nitrobenzenesulfonyl group can be easily removed from the product under a mild condition.

In the invention, the olefin used as a starting material differs between the method for producing an optically active aziridine compound and the method for producing an optically active amine compound. That is, an olefin represented by the formula (III) is used in the method for producing an optically active aziridine compound, while an olefin represented by the formula (VIII) is used in the method for producing an optically active amine compound.

In the olefin represented by the formula (III) according to the method for producing the optically active aziridine compound, $R^4$ is an alkyl group or a substituted alkyl group having a carbon number of 1 to 15, an alkenyl group or a substituted alkenyl group having a carbon number of 2 to 20, an alkynyl group or a substituted alkynyl group having a carbon number of 2 to 20, or an aryl group or a substituted aryl group having a carbon number of 6 to 20. As the alkyl group having a carbon number of 1 to 15, mention may be made of n-hexyl group, ethyl group, n-octyl group and so on. As the alkenyl group having a carbon number of 2 to 20, mention may be made of 1-phenylvinyl group, 2-phenylvinyl group, isopropenyl group and so on. As the alkynyl group having a carbon number of 2 to 20, mention may be made of phenylethynyl group, trimethylsilylethynyl group, cyclohexylethynyl group and so on. As the aryl group having a carbon number of 6 to 20, mention may be made of phenyl group, 2-naphthyl group, p-(1-cyclohexenyl)-phenyl group, p-biphenyl group and so on. Also, $R^5$ is a hydrogen or an alkyl group or a substituted alkyl group having a carbon number of 1 to 10. As the alkyl group is mentioned methyl group or the like. In the $R^4$ and $R^5$, a hydrogen atom in the alkyl group, alkenyl group, alkynyl group and aryl group may be substituted with a halogen atom, a nitro group or the like. Moreover, $R^4$ and $R^5$ may be bonded with each other to form a ring. As the olefin obtained by bonding $R^4$ and $R^5$ with each other to form a ring is mentioned indene (that is a compound wherein $R^4$ is phenyl group, $R^5$ is methyl group and phenyl group is bonded to methyl group) or the like.

On the other hand, in the olefin represented by the formula (VIII) according to the method for producing the optically active amine compound, $R^7$, $R^8$ and $R^9$ are a hydrogen, an alkyl group or a substituted alkyl group having a carbon number of 1 to 20, or an aryl group or a substituted aryl group having a carbon number of 6 to 15, with the proviso that at least one of $R^7$ and $R^8$ is not a hydrogen. As the alkyl group having a carbon number of 1 to 20, mention may be made of methyl group, ethyl group, propyl group, butyl group, isobutyl group and so on. As the aryl group having a carbon number of 6 to 15, mention may be made of phenyl group, 2-methylphenyl group, 2-naphthyl group and so on. Also, $R^{10}$ is an alkyl group or a substituted alkyl group having a carbon number of 1 to 20. As the alkyl group are mentioned methyl group, ethyl group, propyl group, butyl group, isobutyl group and so on. However, $R^7$ and $R^8$ as well as $R^9$ and $R^{10}$ may be bonded with each other to form a ring. In the $R^7$, $R^8$, $R^9$ and $R^{10}$, a hydrogen atom in the alkyl group and aryl group may be substituted with a halogen atom, a nitro group or the like.

Among the olefins represented by the formula (VIII), an olefin represented by the formula (X) is preferable. In the formula (X), each of $R^8$, $R^9$ and $R^{10}$ is the same meaning as mentioned above, and $R^{11}$ is hydrogen or an alkyl group or a substituted alkyl group having a carbon number of 1 to 20. As the alkyl group are mentioned methyl group, ethyl group, propyl group, butyl group, isobutyl group and so on. Moreover, $R^8$ and $R^{11}$ as well as $R^9$ and $R^{10}$ may be bonded with each other to form a ring. For example, when they are bonded with each other to form a 5-member ring or a 6-member ring, the olefin of the formula (X) is represented by the following formula (XIX), (XX), (XXI) or (XXII). However, when both $R^9$ and $R^{10}CH_2$ in the formula (X) are a hydrogen atom, the aziridination proceeds with a high enantioselectivity.

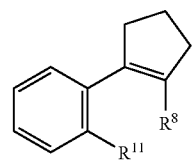

(XIX)

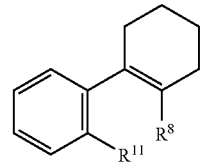

(XX)

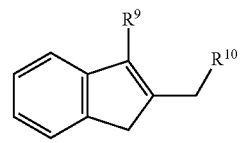

(XXI)

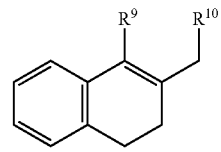

(XXII)

As the olefin represented by the formula (X) are concretely mentioned 1-phenylcyclopentene and 2-ethylindene.

In the method for producing the optically active aziridine compound according to the invention, the olefin represented by the formula (III) is used to produce the aziridine compound represented by the formula (V). On the other hand, in the method for producing the optically active amine compound according to the invention, the olefin represented by the formula (VIII) is used to produce the amine compound represented by the formula (IX). The optically active aziridine compound as a final product in the method for producing the optically active aziridine compound according to the invention is represented by the formula (V), wherein each of $R^4$, $R^5$ and $R^6$ is the same meaning as mentioned above. Moreover, both enantiomers of the optically active aziridine compound can be obtained by properly using the Ru(salen)(CO) complex of the formula (I) and the Ru(salen)(CO) complex of the formula (II). On the other hand, the optically active amine compound as a final product in the method for producing the optically active amine compound according to the invention is represented by the formula (IX), wherein each of $R^6$, $R^7$, $R^8$, $R^9$ and $R^{10}$ is the same meaning as mentioned above. Both enantiomers of the optically active amine compound can be obtained by properly using the Ru(salen)(CO) complex of the formula (I) and the Ru(salen)(CO) complex of the formula (II). These optically active aziridine compounds and amine compounds can be used for the synthesis of medicines and agrochemicals.

In the invention, it is preferable to conduct the asymmetric aziridination or amination reaction in the presence of a zeolite. Although the asymmetric aziridination or amination reaction proceeds with good enatioselectivity without the zeolite, the reaction yield can be largely improved by conducting the reactions in the presence of the zeolite. As the zeolite used in the invention, mention may be made of MS-3A, MS-4A, MS-5A and so on. Among them, MS-4A is preferable. The amount of the zeolite used is within a range of 50 to 500 mg, preferably 100 to 300 mg per 1 mmol of the olefin as a substrate.

The asymmetric aziridination or amination reaction is carried out in a solvent. As the solvent, mention may be made of chlorobenzene, dichloroethane, toluene, dichloromethane and so on. Among them, dichloromethane is preferable. The amount of the solvent used is within a range of 2 to 50 mL, preferably 4 to 10 mL per 1 mmol of the olefin as a substrate.

The aziridination and the amination according to the invention are preferably carried out at −10 to 40° C., and more preferably at room temperature. Since the production method of the invention can be carried out at room temperature, an energy cost for controlling the temperature can be suppressed. In the invention, the optically active aziridine compound or amine compound can be also produced by agitating a mixed solution of the olefin, the sulfonyl azide compound, the solvent and the catalyst. The reaction time is not particularly limited and is properly selected in accordance with the reaction temperature. It is preferable that when the reaction temperature is high, the reaction time is short, while when the reaction temperature is low, the reaction time is long.

The following examples are given in illustration of the invention and are not intended as limitations thereof.

EXAMPLES

Synthesis Example 1 of Complex (aR)-3-formyl-2'-(3,5-difluoro-4-methylphenyl)-2-hydroxy-1,1'-binaphtyl is synthesized according to the following reaction scheme 1.

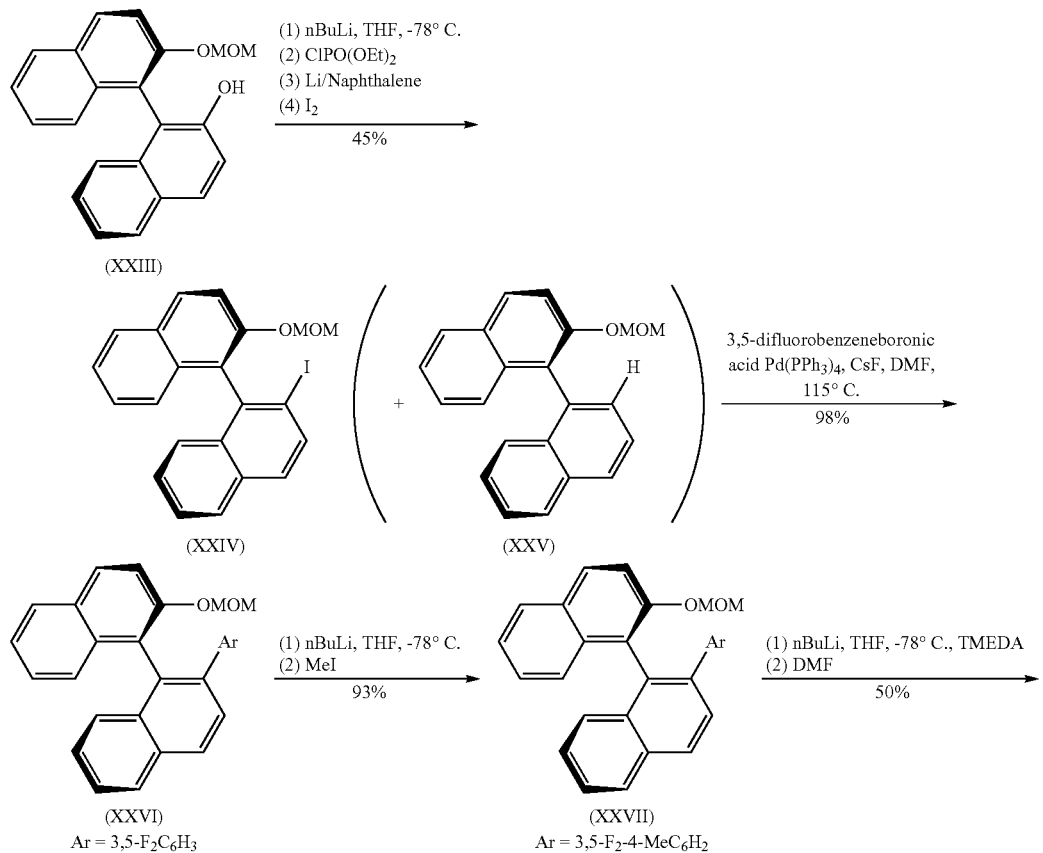

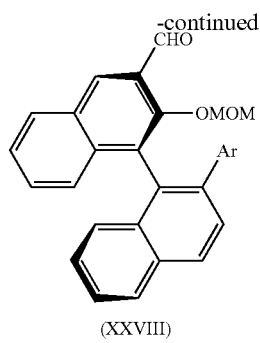 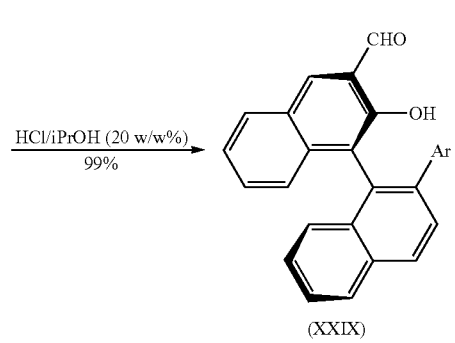

Concretely, the compound represented by the above formula (XXIII) [which is synthesized according to the method described in H. Sasaki, R. Irie, T. Hamada, K. Suzuki, and T. Katsuki, Tetrahedron, 50(41), 11827-11838 (1994)] is dissolved in THF (60 mL) under nitrogen at −78° C. Then, to the solution is added n-butyl lithium (1.58 M, 8.4 mL, 13.2 mmol), which are stirred for 1 hour. To the solution is further added diethyl chlorophosphate (2.1 mL, 13.2 mmol), which is then warmed to room temperature, stirred for 1 hour and cooled to −78° C. again. The resulting mixture is added to a solution of lithium/naphthalene (39.6 mmol, 3.3 eq) in THF (60 mL) and stirred at −78° C. for 1.5 hours. The resulting mixture is treated with iodine (16.7 g, 65.8 mmol, 5.5 eq), stirred for 2 hours, then warmed to room temperature and dried under a reduced pressure. The residue thus obtained is passed through a silica gel column (hexane/toluene=1/0-0/1) to obtain the compound represented by the above formula (XXIV) and the compound represented by the above formula (XXV) at a ratio of 1:1. The resulting mixture is recrystallized from a mixed solution of dichloromethane/hexane to obtain the pure compound of the formula (XXIV) in a yield of 45%. Results of the $^1$H-NMR (400 MHz, CDCl$_3$, 25° C.) to the compound of the formula (XXIV) thus obtained are δ 8.05 (d, J=8.8 Hz, 1H), 8.01 (d, J=7.8 Hz, 1H), 7.90 (m, 2H), 7.67 (d, J=8.8 Hz, 1H), 7.60 (d, J=9.0 Hz, 1H), 7.47 (m, 1H), 7.37 (m, 1H), 7.25 (m, 3H), 6.99 (d, J=8.8 Hz, 1H), 5.11 (ABq, J=7.1 Hz, 2H) and 3.23 (s, 3H), and results of the elemental analysis thereto are H 3.89% and C 60.23% which are well coincident with theoretical values of C$_{22}$H$_{17}$IO (H 3.89% and C 60.02%).

Then, the compound of the formula (XXIV) (1.0 g, 2.27 mmol), Pd(PPh$_3$)$_4$ (131 mg, 0.11 mmol, 5 mol %), cesium fluoride (1.03 g, 6.81 mmol, 3 eq) and 3,5-difluorophenylboronic acid (860 mg, 5.5 mmol, 2.4 eq) are added to N,N-dimethylformamide (DMF, 8 mL). The resulting suspension is heated up to 115° C., stirred for 24 hours and then cooled to room temperature. The resulting mixture is isolated into an ether phase and an aqueous ammonium chloride phase, and the ether phase is dried with anhydrous Na$_2$SO$_4$ and concentrated under a reduced pressure. The residue thus obtained is separated through a chromatography with silica gel (hexane/ethyl acetate=19/1) to obtain the compound represented by the above formula (XXVI) in a yield of 98%. Results of the $^1$H-NMR (400 MHz, CDCl$_3$, 25° C.) to the compound of the formula (XXVI) thus obtained are δ 8.06 (d, J=8.3 Hz, 1H), 7.95 (d, J=8.6 Hz, 2H), 7.86 (d, J=8.8 Hz, 1H), 7.64 (m, 1H), 7.47 (m, 2H), 7.26 (m, 3H), 7.02 (d, J=8.1 Hz, 1H), 6.67 (m, 2H), 6.48 (m, 1H), 4.98 (ABq, J=6.8 Hz, 2H) and 3.13 (s, 3H), and a result of the HRFABMS m/z thereto is 426.1431 which is well coincident with a calculated value of C$_{28}$H$_{20}$F$_2$O$_2$ (M$^+$) (426.1445).

Then, the compound of the formula (XXVI) (938 mg, 2.2 mmol) is dissolved in THF (5.6 mL) under nitrogen at −78° C. To the solution is added n-butyl lithium (1.58 M, 1.4 mL, 2.2 mmol, 1.0 eq) and stirred for 1 hour. To the resulting solution is added iodomethane (415 μL, 6.7 mmol, 3 eq) at −78° C., stirred for 1 hour and then warmed to room temperature. The resulting mixture is quenched with aqueous ammonium chloride and extracted with diethyl ether. The diethyl ether phase is dried with anhydrous Na$_2$SO$_4$ and concentrated under a reduced pressure. The residue thus obtained is separated through a chromatography with silica gel (hexane/ethyl acetate=8/2) to obtain the compound represented by the above formula (XXVII) in a yield of 93%. Results of the $^1$H-NMR (400 MHz, CDCl$_3$, 25° C.) to the compound of the formula (XXVII) thus obtained are δ 8.01 (d, J=8.3 Hz, 1H), 7.95 (d, J=9.3 Hz, 1H), 7.94 (d, J=8.1 Hz, 1H), 7.87 (d, J=9.0 Hz, 1H), 7.80 (d, J=8.3 Hz, 1H), 7.58 (d, J=8.8 Hz, 1H), 7.49 (d, J=8.8 Hz, 1H), 7.23 (m, 5H), 7.02 (d, J=8.3 Hz, 1H), 6.67 (d, J=8.1 Hz), 4.98 (ABq, J=7.0 Hz, 2H), 3.15 (s, 3H) and 2.01 (s, 3H), and results of the elemental analysis thereto are H 5.17% and C 79.11% which are well coincident with theoretical values of C$_{29}$H$_{22}$F$_2$O$_2$ (H 5.03% and C 79.08%).

Then, the compound of the formula (XXVII) (865 mg, 2.0 mmol) is dissolved in THF (5 mL) under nitrogen at −78° C. To the solution are added n-butyl lithium (1.58 M, 1.4 mL, 2.2 mmol, 1.1 eq) and tetramethyletylenediamine (TMEDA, 325 μL, 2.2 mmol, 1.1 eq) and stirred for 1 hour. To the resulting solution is added DMF (750 μL, 9.7 mmol, 4.8 eq) at −78° C., stirred for 1 hour and then warmed to room temperature. The resulting mixture is quenched with water and extracted with diethyl ether. The diethyl ether phase is dried with anhydrous Na$_2$SO$_4$ and concentrated under a reduced pressure. The residue thus obtained is separated through a chromatography with silica gel (hexane/ethyl acetate=8/2) to obtain the compound represented by the above formula (XXVIII) in a yield of 50%. Results of the $^1$H-NMR (400 MHz, CDCl$_3$, 25° C.) to the compound of the formula (XXVIII) thus obtained are δ 10.40 (s, 1H), 8.47 (s, 1H), 8.05 (m, 3H), 8.04 (d, J=8.6 Hz, 1H), 7.97 (m, 2H), 7.60 (d, J=8.6 Hz, 1H), 7.49 (m, 2H), 7.35 (m, 2H), 7.20 (m, 2H), 6.61 (d, J=8.1 Hz, 2H), 4.55 (ABq, J=5.7 Hz, 2H), 2.91 (s, 3H) and 2.01 (s, 3H).

Then, the compound of the formula (XXVIII) (468 mg, 1.0 mmol) is dissolved in hydrochloric acid/isopropanol (20 w/w %, 10 mL) under nitrogen and stirred overnight at room temperature. The resulting mixture is neutralized with aqueous NaHCO$_3$ and then extracted with diethyl ether. The diethyl ether phase is dried with anhydrous Na$_2$SO$_4$ and concentrated under a reduced pressure. The residue thus obtained is separated through a chromatography with silica gel (hexane/ethyl acetate=8/2) to obtain the compound represented by the above formula (XXIX) in a yield of 99%. Results of the $^1$H-NMR (400 MHz, CDCl$_3$, 25° C.) to the compound of the formula (XXIX) thus obtained are δ 10.49 (s, 1H), 10.14 (s, 1H), 8.04 (d, J=8.6 Hz, 1H), 7.97 (d, J=8.3 Hz, 1H), 7.90 (m, 2H), 7.58 (d, J=8.6 Hz, 1H), 7.50 (m, 1H), 7.33 (m, 3H), 7.22 (d, J=8.6 Hz, 1H), 7.03-7.06 (m, 1H), 6.71 (d, J=8.1 Hz, 2H) and 2.00 (s, 1H), and results of the elemental analysis thereto are H 4.53% and C 79.10% which are well coincident with theoretical values of C$_{28}$H$_{18}$F$_2$O$_2$ (H 4.27% and C 79.23%).

Then, (1R,2R)-1,2-diaminocyclohexane [Aldrich Chem. Co.] (10.8 mg, 0.095 mmol) is dissolved in ethanol (1.5 mL). To the solution is added (aR)-3-formyl-2'-(3,5-difluoro-4-methylphenyl)-2-hydroxy-1,1'-binaphtyl represented by the formula (XXIX) (80.5 mg, 0.19 mmol) and stirred at room temperature for 24 hours. After the completion of the reaction, the resulting precipitates are filtered and dried under a reduced pressure at 50° C. for 1 hour to obtain a salen ligand represented by the following formula (XXX) (63.4 mg, yield: 72%).

(XXX)

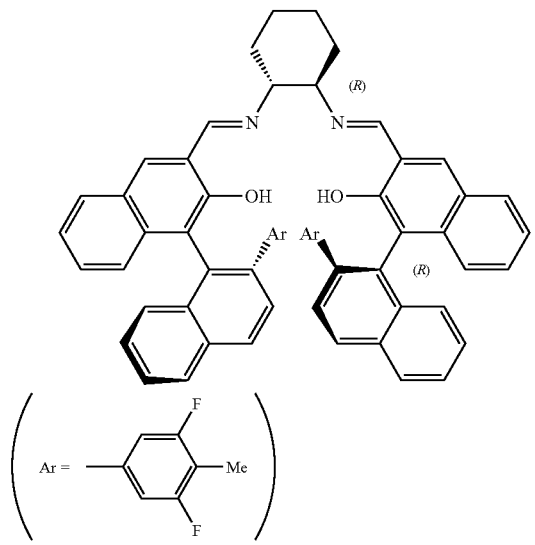

The ligand thus obtained shows characteristic absorptions at 3313, 3055, 2931, 2858, 1631, 1581, 1481, 1342, 1126 and 621 cm$^{-1}$ in an infrared absorption spectrum.

Then, to the dried residue composed of the above salen ligand are added triruthenium dodecacarbonyl [Aldrich Chem. Co.] (57.0 mg, 0.09 mmol) and dehydrated ethanol (2.0 mL) under a nitrogen atmosphere, and the resulting suspension is heated under reflux for 5 days. After the temperature is turned to room temperature again, the mixture is concentrated on a rotary evaporator to remove the solvent. The resulting residue is purified with a silica gel column using dichloromethane/ethanol (=20/1) as a developing solvent to obtain a Ru(salen)(CO) complex represented by the following formula (XXXI) (32.2 mg, yield: 45%).

(XXXI)

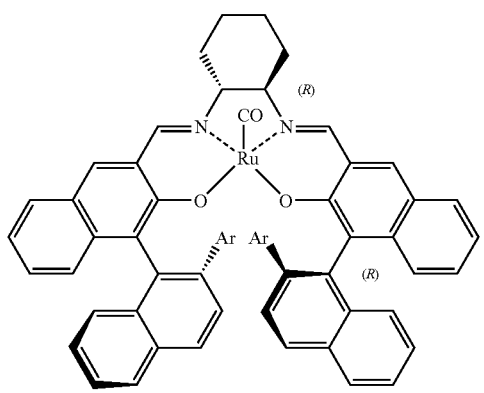

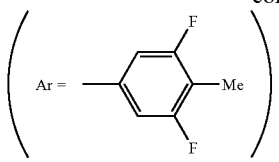

The elementary analysis of the complex thus obtained shows H 4.27%, C 64.09% and N 2.32%, which are well coincident with theoretical values of $C_{63}H_{44}F_4N_2O_3Ru \cdot 1.5H_2O \cdot 1.5CH_2Cl_2$ (H 4.17%, C 64.10% and N 2.32%).

Synthesis Example 2 of Complex (1R,2R)-1,2-Diaminocyclohexane [Aldrich Chem. Co.] (26.3 mg, 0.23 mmol) is dissolved in ethanol (5.0 mL). The solution is added with (aR)-3-formyl-2-hydroxy-2'-[(4-tert-butyldimethylsilyl)phenyl]-1,1'-binaphthyl [which is synthesized according to the method described in H. Sasaki, R. Irie, T. Hamada, K. Suzuki, and T. Katsuki, Tetrahedron, 50(41), 11827-11838 (1994) or the like] (225 mg, 0.46 mmol) and stirred at room temperature for 24 hours. After the completion of the reaction, the resulting precipitates are filtered and dried under a reduced pressure at 50° C. for 1 hour. To the dried residue are added triruthenium dodecacarbonyl [Aldrich Chem. Co.] (150.0 mg, 0.23 mmol) and dehydrated ethanol (5.0 mL) under a nitrogen atmosphere, and the resulting suspension is heated under reflux for 5 days. After the temperature is turned to room temperature again, the resulting mixture is concentrated on a rotary evaporator to remove the solvent. The resulting residue is purified with a silica gel column using dichloromethane/ethanol (=20/1) as a developing solvent to obtain a Ru(salen)(CO) complex represented by the following formula (XXXII) (137.6 mg, yield: 60%).

(XXXII)

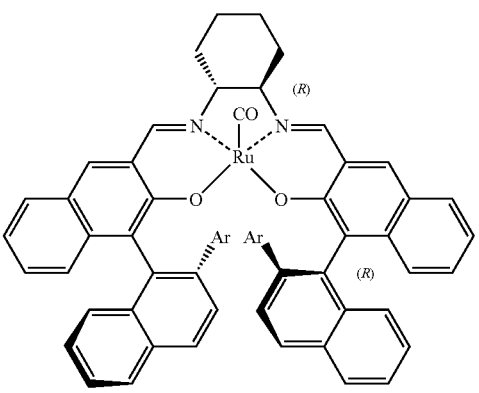

The elementary analysis of the complex thus obtained shows H 5.84%, C 67.40% and N 2.20%, which are well coincident with theoretical values of $C_{73}H_{72}N_2O_3RuSi_2 \cdot 1.0H_2O \cdot 1.5CH_2Cl_2$ (H 5.84%, C 67.38% and N 2.11%).

Synthesis Example 3 of Complex (1R,2R)-1,2-Diaminocyclohexane [Aldrich Chem. Co.] (51.4 mg, 0.45 mmol) is dissolved in ethanol (10 mL). The solution is added with (aR)-3-formyl-2-hydroxy-2'-[(4-tert-butyldiphenylsilyl)phenyl]-1,1'-binaphthyl [which is synthesized according to the method described in H. Sasaki, R. Irie, T. Hamada, K. Suzuki, and T. Katsuki, Tetrahedron, 50(41), 11827-11838 (1994) or the like] (551 mg, 0.9 mmol) and stirred at room temperature for 24 hours. After the completion of the reaction, the resulting precipitates are filtered and dried under a reduced pressure at 50° C. for 1 hour. To the dried residue are added trirutheniumdodecacarbonyl [Aldrich Chem. Co.] (293.5 mg, 0.45 mmol) and dehydrated ethanol (10.0 mL) under a nitrogen atmosphere, and the resulting suspension is heated under reflux for 5 days. After the temperature is turned to room temperature again, the resulting mixture is concentrated on a rotary evaporator to remove the solvent. The resulting residue is purified with a silica gel column using dichloromethane/ethanol (=20/1) as a developing solvent to obtain a Ru(salen)(CO) complex represented by the following formula (XXXIII) (310 mg, yield: 53%).

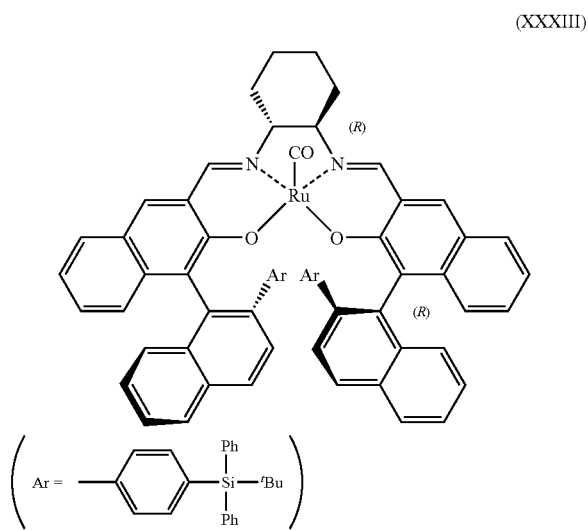

(XXXIII)

The elementary analysis of the complex thus obtained shows H 5.73%, C 74.53% and N 1.84%, which are well coincident with theoretical values of $C_{83}H_{76}N_2O_3RuSi_2.2H_2O$ (H 6.01%, C 74.24% and N 2.09%).

Synthesis Example 4 of Complex (1R,2R)-1,2-Diaminocyclohexane [Aldrich Chem. Co.] (27.5 mg, 0.24 mmol) is dissolved in ethanol (5 mL). To the solution is then added (aR)-3-formyl-2-hydroxy-2'-phenyl-1, 1'-binaphthyl [which is synthesized according to the method described in H. Sasaki, R. Irie, T. Hamada, K. Suzuki, and T. Katsuki, Tetrahedron, 50(41), 11827-11838 (1994) or the like] (179.7 mg, 0.48 mmol) and stirred at room temperature for 24 hours. After the completion of the reaction, the resulting precipitate is filtered and dried under a reduced pressure at 50° C. for 1 hour. To the dried residue are added trirutheniumdodecacarbonyl [Aldrich Chem. Co.] (152.1 mg, 0.24 mmol) and dehydrated ethanol (10 mL) under a nitrogen atmosphere, and the resulting suspension is heated under reflux for 5 days. After the temperature is turned to room temperature again, the resulting mixture is concentrated on a rotary evaporator to remove the solvent. The resulting residue is purified with a silica gel column using dichloromethane/ethanol (=20/1) as a developing solvent to obtain a Ru(salen)(CO) complex represented by the following formula (XXXIV) (80.5 mg, yield: 36%).

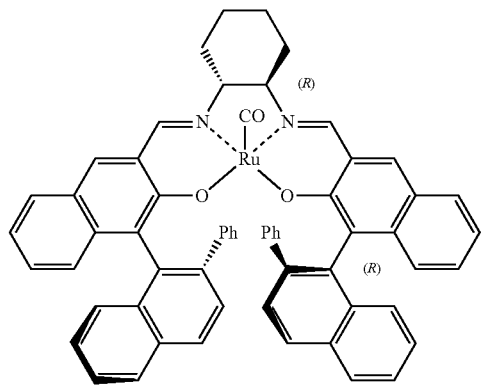

(XXXIV)

The elementary analysis of the complex thus obtained shows H 4.32%, C 65.12% and N 2.35%, which are well coincident with theoretical values of $C_{61}H_{44}N_2O_3Ru.2H_2O.2CH_2Cl_2$ (H 4.52%, C 65.23% and N 2.42%). Moreover, as a result of IR measurement to the complex thus obtained, signals inherent to the complex are observed at 1323.1, 1423.4, 1490.9, 1541.0, 1577.7, 1612.4, 1934.5 and 2019.3 cm$^{-1}$.

Synthesis Example 5 of Complex (aR)-3-Formyl-2'-(3,5-dichloro-4-trimethylsilylphenyl)-2-hydroxy-1,1'-binaphtyl is synthesized according to the following reaction scheme 2.

Scheme 2

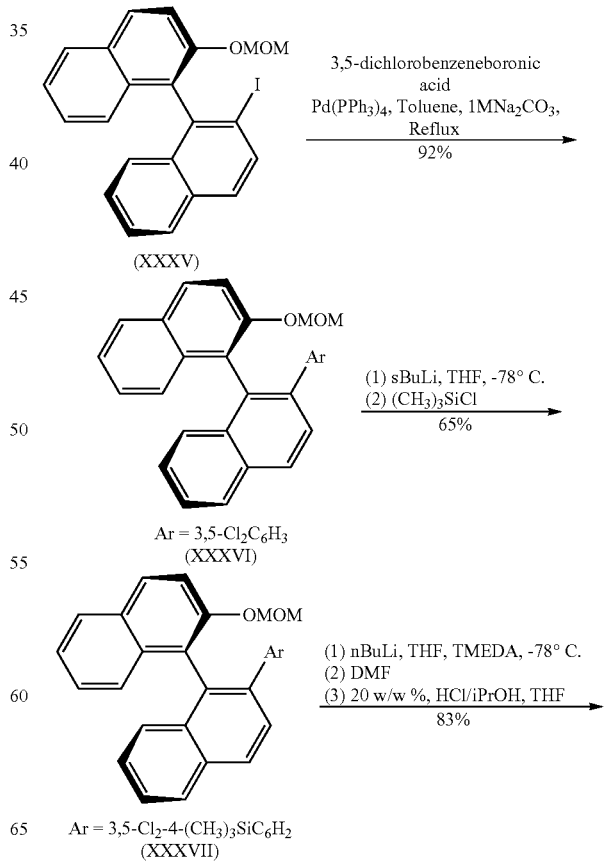

-continued

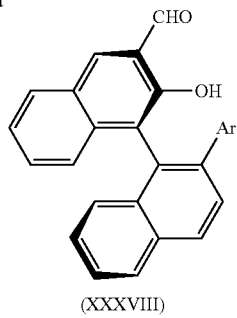

(XXXVIII)

Concretely, the compound represented by the above formula (XXXV) [which is synthesized according to the method described in K. Omura, T. Uchida, R. Irie, and T. Katsuki, Chem. Commun., 2060-2061 (2004)] (194 mg, 0.44 mmol) is dissolved in toluene (3.5 mL) under nitrogen at room temperature, and added with 3,5-dichlorobenzeneboronic acid (232 mg, 0.88 mmol, 2 eq), aqueous sodium carbonate (1 mol/L, 3.5 mL) and tetrakis(triphenylphosphine)palladium (25.5 mg, 22 μmol, 5 mol %). The resulting solution is refluxed for 14 hours and then extracted with ethyl acetate. The ethyl acetate phase is washed with saturated saline, dried with anhydrous sodium sulfate and then concentrated under a reduced pressure. The residue thus obtained is separated through a chromatography with silica gel (hexane/ethyl acetate=30/1) to obtain the compound represented by the above formula (XXXVI) in a yield of 92%. Results of the $^1$H-NMR (400 MHz, CDCl$_3$, 25° C.) to the compound of the formula (XXXVI) thus obtained are δ 8.02 (d, J=8.5 Hz, 1H), 7.96 (d, J=8.3 Hz, 1H), 7.86 (d, J=9.0 Hz, 1H), 7.80 (d, J=8.3 Hz, 1H), 7.58 (d, J=8.5 Hz, 1H), 7.49 (m, 2H), 7.26 (m, 4H), 7.06 (d, J=1.7 Hz, 2H), 7.00 (m, 2H), 5.04 (d, J=7.1 Hz, 1H), 4.96 (d, J=7.1 Hz, 1H) and 3.18 (s, 3H).

Then, the compound of the formula (XXXVI) (335 mg, 0.73 mmol) is dissolved in THF (5 mL) under nitrogen at −78° C. To the solution is added sec-butyl lithium (1.01 mol/L, 1.44 mL, 1.46 mmol, 2 eq) and stirred for 2 hours. To the resulting solution is added trimethylsilylchloride (92.6 μL, 0.73 mmol, 1 eq) at −78° C., stirred for 1 hour and then warmed to room temperature. The resulting mixture is quenched with saturated saline and extracted with ethyl acetate. The organic phase is dried with anhydrous sodium sulfate and concentrated under a reduced pressure. The residue thus obtained is separated through a chromatography with silica gel (hexane/ethyl acetate=40/1) to obtain the compound represented by the above formula (XXXVII) in a yield of 65%. Results of the $^1$H-NMR (400 MHz, CDCl$_3$, 25° C.) to the compound of the formula (XXXVII) thus obtained are δ 8.02 (d, J=8.5 Hz, 1H), 7.95 (d, J=8.1 Hz, 1H), 7.89 (d, J=9.0 Hz, 1H), 7.82 (d, J=8.1 Hz, 1H), 7.59 (d, J=8.5 Hz, 1H), 7.52 (d, J=9.3 Hz, 1H), 7.47 (m, 1H), 7.26 (m, 4H), 7.06 (m, 2H), 7.00 (d, J=8.3 Hz, 1H), 5.04 (d, J=7.1 Hz, 1H), 4.94 (d, J=7.1 Hz, 1H), 3.16 (s, 3H) and 0.38 (s, 9H).

Then, the compound of the formula (XXXVII) (168 mg, 0.32 mmol) is dissolved in THF (2.8 mL) under nitrogen at −78° C. To the solution are added n-butyl lithium (1.60 mol/L, 218 μL, 0.35 mmol, 1.1 eq) and tetramethyletylenediamine (53 μL, 0.35 mmol, 1.1 eq) and stirred for 2 hours. To the resulting solution is added N,N-dimethylformamide (DMF, 27 μL, 0.35 mmol, 1.1 eq) at −78° C., stirred for 1 hour and then warmed to room temperature. The resulting mixture is quenched with saturated saline and extracted with ethyl acetate. The organic phase is dried with anhydrous sodium sulfate and concentrated under a reduced pressure. The residue is dissolved in THF (1.3 mL) and added with hydrogen chloride/isopropyl alcohol (20 w/w %, 0.3 mL) and stirred at room temperature. The resulting mixture is neutralized with saturated aqueous sodium hydrogen carbonate and extracted with ethyl acetate. The organic phase is dried with anhydrous sodium sulfate and concentrated under a reduced pressure. The resulting residue is separated through a chromatography with silica gel (hexane/ethyl acetate=10/1) to obtain the compound represented by the above formula (XXXVIII) in a yield of 83%. Results of the $^1$H-NMR (400 MHz, CDCl$_3$, 25° C.) to the compound of the formula (XXXVIII) thus obtained are δ 10.52 (s, 1H), 10.13 (s, 1H), 8.23 (s, 1H), 8.04 (d, J=8.3 Hz, 1H), 7.96 (d, J=8.1 Hz, 1H), 7.90 (dd, J=7.6 Hz, J=1.7 Hz, 1H), 7.58 (d, J=8.5 Hz, 1H), 7.50 (dd, J=7.8 Hz, J=6.8 Hz, 1H), 7.34 (m, 3H), 7.22 (m, 1H), 7.11 (s, 2H), 7.02 (d, J=9.3 Hz, 1H) and 0.37 (s, 9H).

(1R,2R)-1,2-diaminocyclohexane [Aldrich Chem. Co.] (16.0 mg, 0.14 mmol) is dissolved in ethanol (3 mL) and added with (aR)-3-formyl-2'-(3,5-dichloro-4-trimethylsilylphenyl)-2-hydroxy-1,1'-binaphtyl (132.2 mg, 0.26 mmol) and stirred at room temperature for 24 hours. After the completion of the reaction, the resulting precipitates are filtered and dried under a reduced pressure at 50° C. for 1 hour to obtain a salen ligand represented by the following formula (XXXIX) in a yield of 82%. Results of the $^1$H-NMR (400 MHz, CDCl$_3$, 25° C.) to the compound of the formula (XXXIX) thus obtained are δ13.33 (s, 2H), 8.45 (s, 2H), 8.02 (d, J=8.5 Hz, 2H), 7.95 (d, J=8.1 Hz, 2H), 7.67 (m, 4H), 7.58 (d, J=8.3 Hz, 2H), 7.42 (m, 2H), 7.19 (m, 10H), 6.97 (ddd, J=7.1 Hz, J=6.8 Hz, J=1.3 Hz, 2H), 6.85 (d, J=7.6 Hz, 2H), 3.72 (m, 1H), 3.33 (m, 1H), 1.91 (m, 4H), 1.72 (m, 2H), 1.45 (m, 2H) and 0.35 (s, 18H).

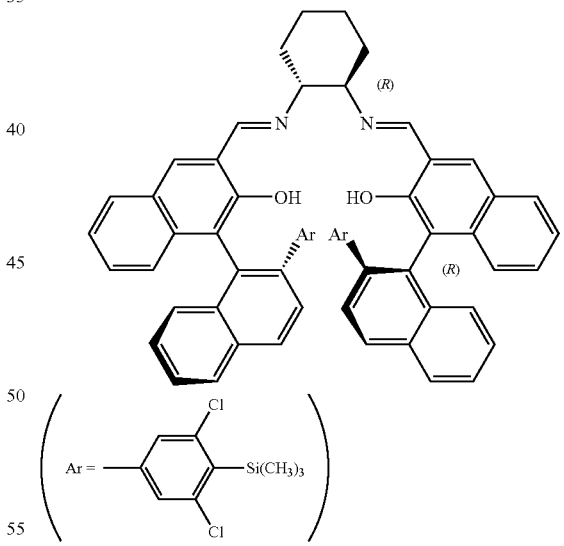

(XXXIX)

Then, to the salen ligand represented by the formula (XXXIX) (91.8 mg, 0.08 mmol) are added trirutheniumdodecacarbonyl [Aldrich Chem. Co.] (68.8 mg, 0.11 mmol) and dehydrated ethanol (7 mL) under a nitrogen atmosphere, and the resulting suspension is heated under reflux for 24 hours. Then, the resulting mixture is turned to room temperature again and concentrated on a rotary evaporator to remove the solvent. The resulting residue is purified with a silica gel column (hexane/ethyl acetate=5/1) to obtain a Ru(salen)(CO) complex represented by the following formula (XL) (63.7 mg, yield: 62%). The elementary analysis of the complex thus obtained shows H 4.87%, C 63.80% and N 2.10%, which are well coincident with theoretical values of $C_{67}H_{56}Cl_4N_2O_3RuSi_2 \cdot 1.5H_2O$ (H 4.71%, C 63.70% and N 2.22%).

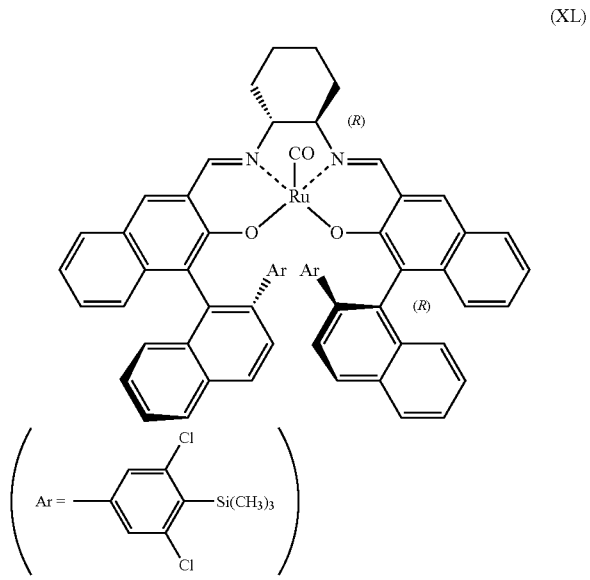

(XL)

Example 1

A solution of the Ru(salen)(CO) complex represented by the formula (XXXI) (1.0 mg, 0.9 μmol) in toluene (0.25 mL) is concentrated twice azeotropically under vacuum. To the concentrated residue are added MS-4A (20 mg), styrene (104 mg, 1.0 mmol) and 2-bromonaphthalene (40 mg, as an internal standard) and further added dichloromethane (0.5 mL). The resulting suspension is stirred at room temperature for 0.5 hours, and then added with p-toluenesulfonyl azide (155 μL, 1.0 mmol) and further stirred for 24 hours. After the completion of the reaction, as a yield of the corresponding aziridine compound is measured by $^1$H-NMR (400 MHz), it is 78%. Also, as the enantiomeric excess of the aziridine compound is analyzed by a high performance liquid chromatography using a DAICEL CHIRALCEL OJ-H column and a mixed solution of hexane/isopropanol (=1/1), the enantiomeric excess is 85% ee. Moreover, an absolute configuration of the product is determined by comparison with the specific rotation described in M. Shi. C.-J. Wang, Chirality, 2002, 14, 412-416. The results are shown in Table 1.

Examples 2-5

The aziridination is carried out in the same manner as in Example 1 except that each of olefins shown in Table 1 is used instead of styrene. Moreover, the enantiomeric excess is analyzed by the high performance liquid chromatography using a DAICEL CHIRALPAK AS-H and a mixed solution of hexane/isopropanol (=2/1) in Example 2, a DAICEL CHIRALPAK AD-H and a mixed solution of hexane/isopropanol (=2/1) in Example 3, a DAICEL CHIRALCEL OF and a mixed solution of hexane/isopropanol (=2/1) in Example 4, and a DAICEL CHIRALPAK AS-H and a mixed solution of hexane/isopropanol (=7/3) in Example 5. The results are shown in Table 1.

Examples 6-7

The aziridination is carried out in the same manner as in Example 1 except that each of olefins shown in Table 1 is used instead of styrene and the amount of the Ru(salen)(CO) complex represented by the formula (XXXI) used is 2 mol %. Moreover, the enantiomeric excess is analyzed by the high performance liquid chromatography using a DAICEL CHIRALPAK AS-H and a mixed solution of hexane/isopropanol (=9/1) in Example 6, and a DAICEL CHIRALPAK AD and a mixed solution of hexane/isopropanol (=15/1) in Example 7. An absolute configuration of the product in Example 7 is confirmed to be 1S, 2R by comparison with the specific rotation described in M. Shi. C.-J. Wang, Chirality, 2002, 14, 412-416. The results are shown in Table 1.

Examples 8-11

The aziridination is carried out in the same manner as in Example 1 except that each of complexes and olefins shown in Table 1 is used. Moreover, the amount of the complex used is 0.1 mol % in Examples 8-10 and the amount of the complex used is 2.0 mol % in Example 11. Furthermore, the enantiomeric excess is analyzed by the high performance liquid chromatography using a DAICEL CHIRALPAK AS-H and a mixed solution of hexane/isopropanol (=2/1) in Example 10, and a DAICEL CHIRALPAK AS-H and a mixed solution of hexane/isopropanol (=9/1) in Example 11. The results are shown in Table 1.

Example 12

The Ru(salen)(CO) complex represented by the formula (XL) (0.6 mg, 0.5 μmol) is dissolved in toluene (0.25 mL) and dried twice azeotropically under vacuum. To the residue are added Molecular Sieves 4A (MS-4A, 10 mg), styrene (57 μL, 0.5 mmol) and 2-bromonaphthalene (20 mg, as an internal standard) and further added dichloromethane (0.25 mL) to prepare a suspension. The suspension is stirred at room temperature for 0.5 hours, and then added with p-toluenesulfonyl azide (78 μL, 0.5 mmol) and further stirred for 12 hours. After the completion of the reaction, the resulting solution is filtered and the filtrate is concentrated under a reduced pressure. The resulting residue is separated through a chromatography with silica gel (hexane/ethyl acetate=10/1) to obtain the corresponding aziridine compound in a yield of 93%. Moreover, as an enantiomeric excess of the aziridine compound is analyzed by a high performance liquid chromatography using a DAICEL CHIRALCEL OJ-H column and a mixed solution of hexane/isopropyl alcohol (=1/1), it is 86% ee. The results are shown in Table 1.

Examples 13-15

The aziridination is carried out in the same manner as in Example 12 except that each of olefins shown in Table 1 is used instead of styrene. Moreover, the analysis is carried out by the high performance liquid chromatography using a DAICEL CHIRALCEL OJ-H column and a mixed solution of hexane/isopropyl alcohol (=9/1) in Example 13, a DAICEL CHIRALCEL OF column and a mixed solution of hexane/isopropyl alcohol (=2/1) in Example 14 and a DAICEL CHIRALCEL OJ-H column and a mixed solution of hexane/isopropyl alcohol (=19/1) in Example 15. The results are shown in Table 1.

Examples 16-17

The aziridination is carried out in the same manner as in Example 12 except that each of olefins shown in Table 1 is used instead of styrene, the amount of the Ru(salen)(CO) complex represented by the formula (XL) used is 2 mol % and the reaction mixture is stirred for 38 hours. Moreover, the analysis is carried out by the high performance liquid chromatography using a DAICEL CHIRALPAK AS-H column and a mixed solution of hexane/isopropyl alcohol (=19/1) in Example 16, and a DAICEL CHIRALPAK AD-H column and a mixed solution of hexane/isopropyl alcohol (=19/1) in Example 17. The results are shown in Table 1.

Comparative Example 1

The aziridination is carried out in the same manner as in Example 1 except that the Ru(salen)(CO) complex represented by the formula (XXXIV) (2.0 μmol) is used instead of the Ru(salen)(CO) complex represented by the formula (XXXI) (0.9 μmol). The results are shown in Table 1.

produce the various optically active aziridine compound corresponding to the respective olefins. Moreover, as seen from the comparison between Example 1 and Comparative example 1, the turnover number of the Ru(salen)(CO) complex according to the invention is considerably higher than that of the conventional Ru(salen)(CO) complex.

Example 18

The azeotropically dried Ru(salen)(CO) complex represented by the formula (XXXI) (4.3 mg, 4 μmol) is placed in a Schlenk tube and purged with nitrogen. Then, MS4A (20 mg), styrene (10.4 mg, 0.1 mmol) and 2-bromonaphthalene (4.0 mg, as an internal standard) are added to the tube and dichloromethane (0.5 mL) is further added. The resulting suspension is stirred at room temperature for 0.5 hours, and

TABLE 1

| | Catalyst | Olefin | Yield (%) | Enantiomeric excess (% ee) | TON | Configuration |
|---|---|---|---|---|---|---|
| Example 1 | Formula (XXXI) | $C_6H_5$—CH=$CH_2$ | 78 | 85 | 867 | S |
| Example 2 | Formula (XXXI) | p-Br$C_6H_4$—CH=$CH_2$ | 79 | 90 | 878 | — |
| Example 3 | Formula (XXXI) | p-$O_2$N$C_6H_4$—CH=$CH_2$ | 34 | 87 | 378 | — |
| Example 4 | Formula (XXXI) | 2-$C_{10}H_7$—CH=$CH_2$ | 65 | 87 | 722 | — |
| Example 5 | Formula (XXXI) | $C_6H_5$C≡C—CH=$CH_2$ | 61 | 96 | 678 | — |
| Example 6 | Formula (XXXI) | n-$C_6H_{13}$—CH=$CH_2$ | 20 | 86 | 10 | — |
| Example 7 | Formula (XXXI) | indene | 36 | >99 | 18 | 1S,2R |
| Example 8 | Formula (XXXII) | $C_6H_5$—CH=$CH_2$ | 41 | 87 | 410 | S |
| Example 9 | Formula (XXXIII) | $C_6H_5$—CH=$CH_2$ | 23 | 87 | 230 | S |
| Example 10 | Formula (XXXII) | p-Br$C_6H_4$—CH=$CH_2$ | 33 | 90 | 330 | — |
| Example 11 | Formula (XXXII) | n-$C_6H_{13}$—CH=$CH_2$ | 30 | 86 | 15 | — |
| Example 12 | Formula (XL) | $C_6H_5$—CH=$CH_2$ | 93 | 86 | 930 | — |
| Example 13 | Formula (XL) | p-Br$C_6H_4$—CH=$CH_2$ | 91 | 90 | 910 | — |
| Example 14 | Formula (XL) | 2-$C_{10}H_7$—CH=$CH_2$ | 90 | 82 | 900 | — |
| Example 15 | Formula (XL) | $C_6H_5$C≡C—CH=$CH_2$ | 90 | 96 | 900 | — |
| Example 16 | Formula (XL) | n-$C_6H_{13}$—CH=$CH_2$ | 63 | 79 | 32 | — |
| Example 17 | Formula (XL) | indene | 48 | >99 | 24 | — |
| Comparative Example 1 | Formula (XXXIV) | $C_6H_5$—CH=$CH_2$ | 71 | 87 | 36 | S |

The reaction scheme corresponding to Examples 1-6 and 8-16 in Table 1 is shown below.

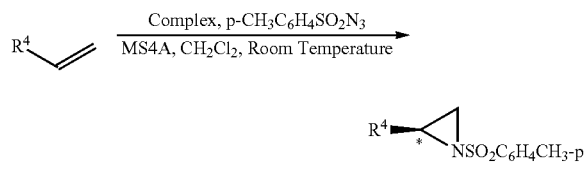

The reaction scheme corresponding to Examples 7 and 17 is shown below.

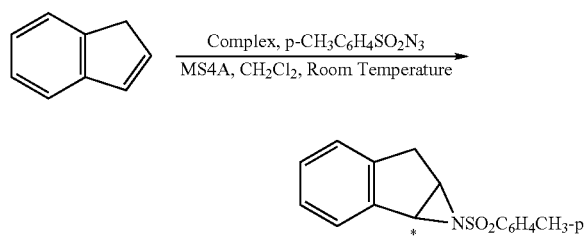

As seen from the results in Table 1, the method according to the invention can be applied to various olefins and can then added with p-nitrobenzenesulfonyl azide (22.8 mg, 0.1 mmol) and further stirred for 24 hours. After the completion of the reaction, as the yield of the corresponding aziridine compound is measured by $^1$H-NMR (400 MHz), it is 100%. Moreover, as an enantiomeric excess of the aziridine compound is analyzed by a high performance liquid chromatography using a DAICEL CHIRALCEL OD-H column and a mixed solution of hexane/isopropanol (=8/2), the enantiomeric excess is 84% ee. The results are shown in Table 2.

Examples 19-21 and Comparative Example 2

The aziridination is carried out in the same manner as in Example 18 by using each of complexes and olefins shown in Table 2. Moreover, the amount of the complex used is 1 mol % based on the olefin as the substrate in Example 19 and the amount of the complex used is 4 mol % based on the olefin as the substrate in Examples 20-21 and Comparative example 2. Furthermore, the enantiomeric excess is analyzed by the high performance liquid chromatography using a DAICEL CHIRALCEL OD-H and a mixed solution of hexane/isopropanol (=1/1) in Example 20, and a DAICEL CHIRALCEL OD-H and a mixed solution of hexane/isopropanol (=2/1) in Example 21. The results are shown in Table 2.

TABLE 2

| | Catalyst | Olefin | Yield (%) | Enantiomeric excess (% ee) | TON | Configuration |
|---|---|---|---|---|---|---|
| Example 18 | Formula (XXXI) | $C_6H_5$—CH=$CH_2$ | 100 | 84 | — | S |
| Example 19 | Formula (XXXI) | $C_6H_5$—CH=$CH_2$ | 34 | 84 | 34 | S |
| Example 20 | Formula (XXXI) | $C_6H_5$C≡C—CH=$CH_2$ | 100 | 90 | — | — |
| Example 21 | Formula (XXXI) | p-$BrC_6H_4$—CH=$CH_2$ | 66 | 81 | — | — |
| Comparative Example 2 | Formula (XXXIV) | $C_6H_5$—CH=$CH_2$ | 22 | 82 | 5 | S |

The reaction scheme corresponding to Examples 18-21 in Table 2 is shown below.

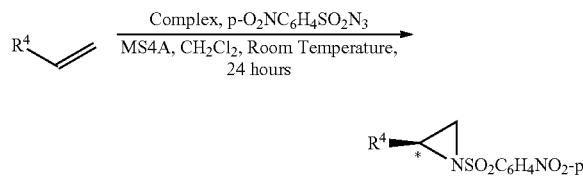

As seen from the results in Table 2, p-nitrobenzenesulfonyl azide, which was difficult to be used as a nitrene precursor in the conventional technique, can be used in the method according to the invention. Also, as seen from the comparison between Example 19 and Comparative example 2, the turnover number of the Ru(salen)(CO) complex according to the invention is much higher than that of the conventional Ru(salen)(CO) complex.

Example 22

The Ru(salen)(CO) complex represented by the formula (XL) (0.6 mg, 0.5 μmol) is dissolved in toluene (0.25 mL) and dried twice azeotropically under vacuum. To the residue are added Molecular Sieves 4A (MS-4A, 10 mg), styrene (5.7 μL, 0.05 mmol) and 2-bromonaphthalene (2.0 mg, as a internal standard) and further added dichloromethane (0.25 mL) to prepare a suspension. The suspension is stirred at room temperature for 0.5 hours, cooled to 0° C. and then added with 2-(trimethylsilyl)ethanesulfonyl azide (9.6 μL, 0.05 mmol) and further stirred at 0° C. for 12 hours. After the completion of the reaction, the resulting solution is filtered and the filtrate is concentrated under a reduced pressure. The resulting residue is separated through a chromatography with silica gel (hexane/ethyl acetate=10/1) to obtain the corresponding aziridine compound in a yield of 99%. Moreover, as an enantiomeric excess of the aziridine compound is analyzed by a high performance liquid chromatography using a DAICEL CHIRALCEL OJ-H column and a mixed solution of hexane/isopropyl alcohol (=97/3) as an eluent, it is 92% ee. The results are shown in Table 3.

Examples 23-24

The aziridination is carried out in the same manner as in Example 22 except that each of olefins shown in Table 3 is used instead of styrene. Moreover, the analysis is carried out by the high performance liquid chromatography using a DAICEL CHIRALCEL OJ-H column and a mixed solution of hexane/isopropyl alcohol (=9/1) in Examples 23-24. The results are shown in Table 3.

TABLE 3

| | Catalyst | Olefin | Yield (%) | Enantiomeric excess (% ee) | TON |
|---|---|---|---|---|---|
| Example 22 | Formula (XL) | $C_6H_5$—CH=$CH_2$ | 99 | 92 | 99 |
| Example 23 | Formula (XL) | p-$BrC_6H_4$—CH=$CH_2$ | 76 | 92 | 76 |
| Example 24 | Formula (XL) | $C_6H_5$C≡C—CH=$CH_2$ | 50 | >99 | 50 |

The reaction scheme corresponding to Examples 22-24 in Table 3 is shown below.

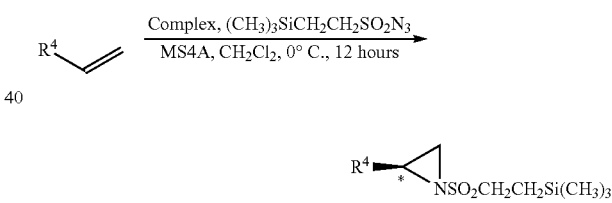

As seen from the results in Table 3, a substituted or non-substituted alkylsulfonyl azide, which was difficult to be used as a nitrene precursor in the conventional technique, can be used in the method according to the invention.

Example 25

The reaction is carried out in the same manner as in Example 1 except that 2-ethylindene is used instead of styrene. Moreover, the enantiomeric excess is analyzed by the high performance liquid chromatography using a DAICEL CHIRALCEL OD-H column and a mixed solution of hexane/isopropanol (=1/1) in this Example. The results are shown in Table 4.

Comparative Example 3

The reaction is carried out in the same manner as in Example 25 except that the Ru(salen)(CO) complex of the formula (XXXIV) is used instead of the Ru(salen)(CO) complex of the formula (XXXI). The results are shown in Table 4.

TABLE 4

| | Substrate | Product | Yield (%) | Enantiomeric Excess (% ee) |
|---|---|---|---|---|
| Example 25 | (structure) | *NHSO₂C₆H₄CH₃-p (structure) | 32 | 84 |
| Comparative Example 3 | | | 17 | 80 |

As seen from the results in Table 4, the olefin having E-substituent as shown by the formula (VIII) can be aminated with the sulfonyl azide compound in the presence of the Ru(salen)(CO) complex to obtain an optically active amine compound. Also, as seen from the comparison between Example 25 and Comparative Example 3, the Ru(salen)(CO) complex according to the invention can improve a yield as compared with the conventional Ru(salen)(CO) complex. This is considered due to the improvement of the turnover number.

Examples 26-27

The reaction is carried out in the same manner as in Example 18 except that 1-phenylcyclopentene or 2-ethylindene is used instead of styrene. Moreover, the enantiomeric excess is analyzed by the high performance liquid chromatography using a DAICEL CHIRALCEL OD-H column and a mixed solution of hexane/isopropanol (=2/1) in Example 26 and a DAICEL CHIRALCEL OD-H column and a mixed solution of hexane/isopropanol (=1/1) in Example 27. The results are shown in Table 5.

TABLE 5

| | Substrate | Product | Yield (%) | Enantiomeric Excess (% ee) |
|---|---|---|---|---|
| Example 26 | Ph (cyclopentene) | Ph (cyclopentene with *NHSO₂C₆H₄NO₂-p) | 53 | 61 |
| Example 27 | (2-ethylindene) | (indene with *NHSO₂C₆H₄NO₂-p) | 12 | 73 |

As seen from the results in Table 5, the various olefins having E-substituent can be aminated with the sulfonyl azide compound in the presence of the Ru(salen)(CO) complex to obtain an optically active amine compound.

INDUSTRIAL APPLICABILITY

The production method according to the invention is very useful to produce an optically active aziridine compound or amine compound by subjecting an olefin to an enantioselective aziridination or amination. Also, the complex according to the invention is useful as a catalyst for the production method. Furthermore, the intermediate and the salen ligand according to the invention are useful for the synthesis of the catalyst. Moreover, the optically active aziridine compound and amine compound obtained according to the production method of the invention can be used for the synthesis of medicines and agrochemicals.

The invention claimed is:

1. A Ru(salen)(CO) complex represented by the following formula (I) or (II):

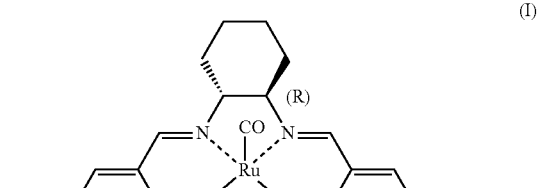

(I)

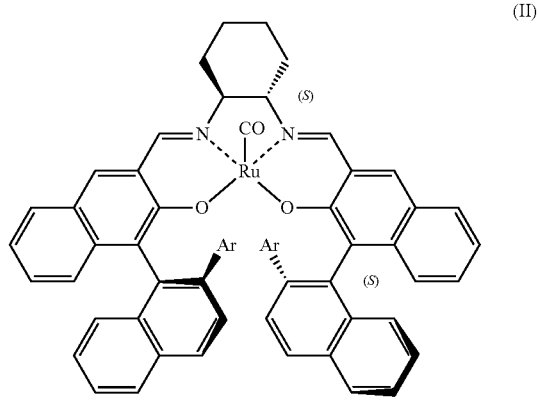

(II)

in the formulae (I) and (II), Ar is represented by the following formula (VI) or (VII):

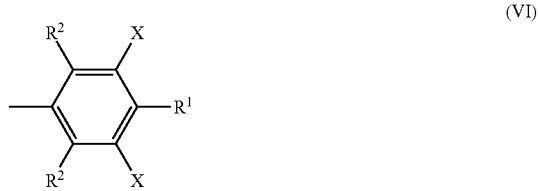

(VI)

(VII)

in the formula (VI), Xs are independently a halogen or a halogenated alkyl group, and $R^1$ and $R^2$s are independently a hydrogen or an alkyl group or a trialkylsilyl group having a carbon number of 1 to 4, and in the formula (VII), $R^3$ is a group formed by bonding three alkyl groups or aryl groups to carbon or silicon.

2. A Ru(salen)(CO) complex represented by the formula (I) or (II) according to claim 1, wherein Ar is represented by the formula (VI), in which Xs are fluorine or chlorine, $R^1$ is a methyl group or a trimethylsilyl group and $R^2$s are hydrogen.

3. A Ru(salen)(CO) complex represented by the formula (I) or (II) according to claim 1, wherein Ar is represented by the formula (VII), in which $R^3$ is a group formed by bonding three alkyl groups or aryl groups to carbon or silicon.

4. A salen ligand represented by the following formula (XVII) or (XVIII):

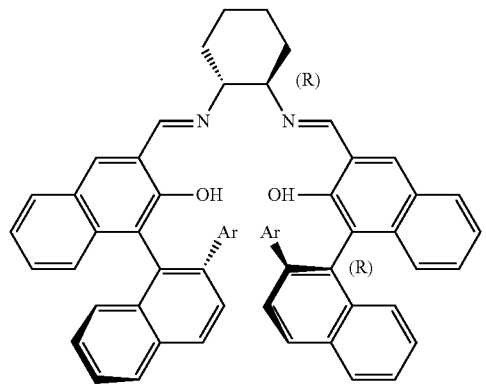

(XVII)

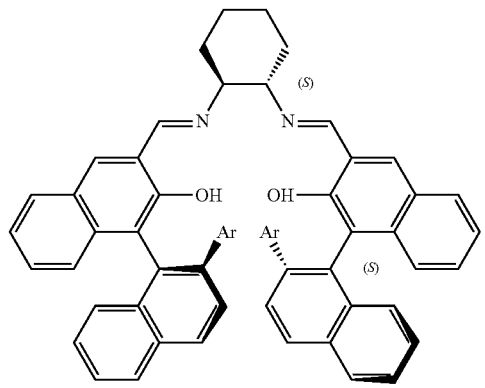

(XVIII)

in the formulae (XVII) and (XVIII), Ar is represented by the following formula (VI)

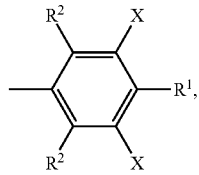

(VI)

in the formula (VI), Xs are independently a halogen or a halogenated alkyl group, and $R^1$ and $R^2$s are independently a hydrogen or an alkyl group or a trialkylsilyl group having a carbon number of 1 to 4.

* * * * *